United States Patent
Pakrul et al.

(10) Patent No.: US 11,786,626 B2
(45) Date of Patent: Oct. 17, 2023

(54) AUTOMOTIVE AIR PURIFIER

(71) Applicants: Matthew H. Pakrul, Johnson City, TN (US); Daniel R. Schumaier, Elizabethton, TN (US)

(72) Inventors: Matthew H. Pakrul, Johnson City, TN (US); Daniel R. Schumaier, Elizabethton, TN (US)

(73) Assignee: Matthew Pakrul, Johnson City, TN (US)

( * ) Notice: Subject to any disclaimer, the term of this patent is extended or adjusted under 35 U.S.C. 154(b) by 232 days.

(21) Appl. No.: 17/479,046

(22) Filed: Sep. 20, 2021

(65) Prior Publication Data
US 2023/0086014 A1  Mar. 23, 2023

(51) Int. Cl.
*A61L 9/20* (2006.01)
*B60H 3/00* (2006.01)

(52) U.S. Cl.
CPC .............. *A61L 9/20* (2013.01); *B60H 3/0078* (2013.01); *A61L 2209/12* (2013.01)

(58) Field of Classification Search
None
See application file for complete search history.

(56) References Cited

U.S. PATENT DOCUMENTS

| 9,974,881 | B2* | 5/2018 | Kim | A61L 9/205 |
| 10,112,461 | B2* | 10/2018 | Kim | B60H 1/00521 |
| 2007/0053188 | A1* | 3/2007 | New | B60Q 3/43 362/276 |
| 2017/0217284 | A1* | 8/2017 | Ji | B60H 1/00821 |

FOREIGN PATENT DOCUMENTS

| WO | 02066272 A2 | 8/2002 | |
| WO | WO-02066272 A2 * | 8/2002 | B60H 1/34 |
| WO | WO-02066272 A3 * | 2/2003 | B60H 1/34 |

* cited by examiner

*Primary Examiner* — Andrew Smyth
(74) *Attorney, Agent, or Firm* — Luedeka Neely Group, P.C.

(57) ABSTRACT

An air purifier for use in a vehicle having louvered air vents includes a housing having rear and front air flow openings that are aligned with and in air flow communication with each other. A louver clip is attached to the housing adjacent the rear air flow opening. The louver clip is configured to engage a louver on an air vent in the vehicle to hold the housing in place in front of the air vent. The air purifier includes an annular ultraviolet light bulb having a central air flow opening aligned with the front and rear air flow openings in the housing. An annular ultraviolet reflector at least partially encircles the annular ultraviolet light bulb. The air purifier includes a power source for providing electrical power to the ultraviolet light bulb, and a power switch for turning power on or off to the ultraviolet light bulb.

9 Claims, 5 Drawing Sheets

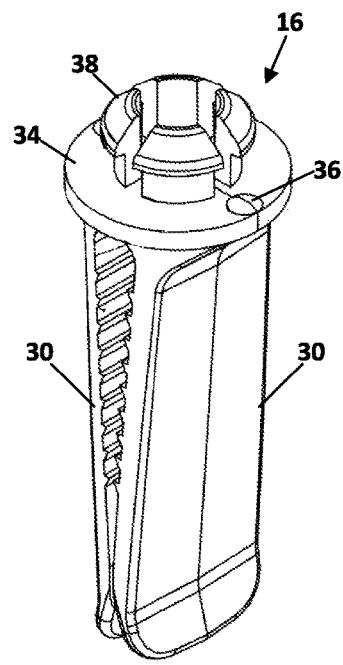
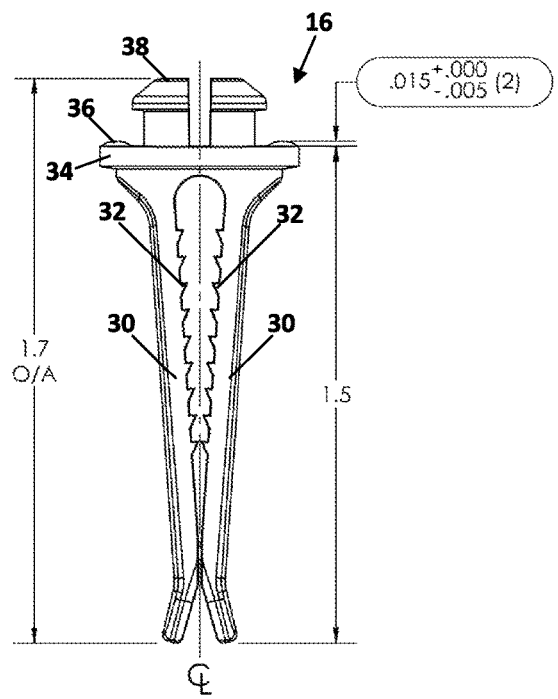
*FIG. 5A*  *FIG. 5B*
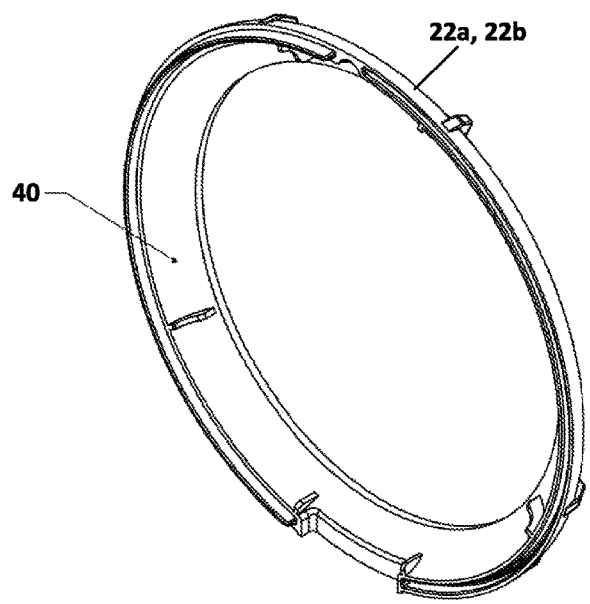
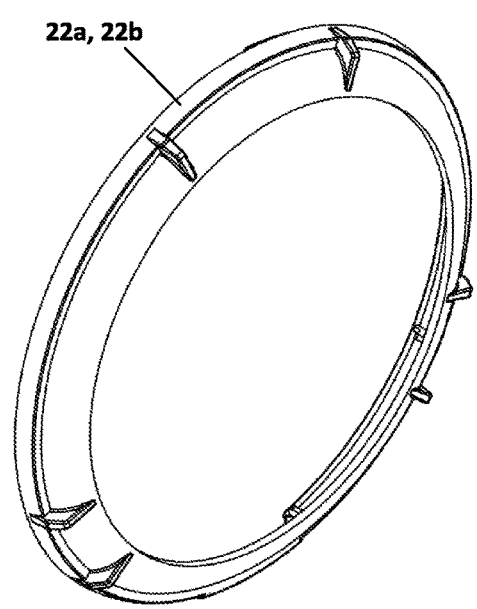
*FIG. 6A*  *FIG. 6B*

AUTOMOTIVE AIR PURIFIER

FIELD

This disclosure relates to the field of air purification. More particularly, this disclosure relates to a device for purifying air within the cabin of an automobile.

BACKGROUND

The maintenance of clean healthy air in small enclosed environments is critical to preserve the health of the occupants of such environments. For example, occupants in a vehicle such as an automobile share the air in the interior of the vehicle cabin. In such a shared space, an occupant may breathe in air that was previously breathed in and expelled by another occupant. If any occupant is infected by a viral microorganism, that occupant may shed the microorganism in the expelled breath, which may in turn infect another occupant in the vehicle. This is more likely to happen if the air in the vehicle is not being constantly replaced by fresh air, such as is the case when the vehicle windows are closed to maintain a comfortable temperature within the vehicle when the exterior air is uncomfortably cold or hot.

Although some vehicles include factory-installed cabin filters, such particulate filters are not effective in capturing viral microorganisms. Current after-market air filter systems are also not effective for this purpose.

What is needed, therefore, is an air purification system that is effective in eliminating viral microorganisms in the air circulating within the cabin of a vehicle.

SUMMARY

The above and other needs are met by an air purifier for use in a vehicle having louvered air vents. Preferred embodiments of the air purifier include a housing and a louver clip attached to the housing. The housing has rear and front air flow openings that are aligned with and in air flow communication with each other. The louver clip is configured to engage a louver on an air vent in the vehicle so as to hold the housing in place in front of the louvered air vent. The air purifier includes an annular ultraviolet (UV) light bulb disposed within the housing. The UV bulb has a central air flow opening aligned with the front and rear air flow openings in the housing. An annular ultraviolet reflector is disposed within the housing that at least partially encircles the annular ultraviolet light bulb. A power source disposed within the housing provides electrical power to the ultraviolet light bulb. A power switch disposed within the housing is used to turn power on or off to the ultraviolet light bulb.

In some preferred embodiments, the front and rear air flow openings in the housing are circular, and the housing includes a plurality of front radial vent spokes that span the front air flow opening in a radial pattern, wherein the front air flow opening is divided by the front radial vent spokes into a plurality of front air flow channels. The housing also includes a plurality of rear radial vent spokes that span the rear air flow opening in a radial pattern, wherein the rear air flow opening is divided by the rear radial vent spokes into a plurality of rear air flow channels.

In some preferred embodiments, the air purifier includes a rear hub having a central aperture that is centrally disposed in the rear air flow opening of the housing, and the proximal ends of the plurality of rear radial vent spokes terminate in the rear hub. The louver clip includes a flange and a plurality of prongs extending forward of the flange. The prongs are operable to flex inward as tips of the prongs are pressed into the central aperture of the rear hub. The prongs are operable to snap outward to secure the louver clip against the rear hub as the tips of the prongs pass through the central aperture.

In some preferred embodiments, the louver clip includes a flange with a pair of opposing jaws extending rearward of the flange. The opposing jaws are operable to flex outward away from each other to engage and clamp onto the louver in one of the air vents in the vehicle.

In some preferred embodiments, the annular ultraviolet reflector has a UV-reflective coating on inner surfaces thereof.

In some preferred embodiments, the annular ultraviolet reflector includes front and rear reflector portions, and the annular UV light bulb is sandwiched between the front and rear reflector portions.

In some preferred embodiments, the air purifier includes a plurality of ribs molded into inner surfaces of the front and rear reflector portions. The ribs keep the annular UV light bulb secured and centered between the front and rear reflector portions.

In some preferred embodiments, the housing includes a front housing portion in which the front air flow opening is disposed and a rear housing portion in which the rear air flow opening is disposed, wherein the front and rear housing portions are operable to snap together to form the housing.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIGS. 5A and 5B depict a louver clip of an automotive air purifier according to an embodiment of the invention;

FIGS. 6A and 6B depict rear and front UV reflectors of an automotive air purifier according to an embodiment of the invention;

DETAILED DESCRIPTION

Figure 3:
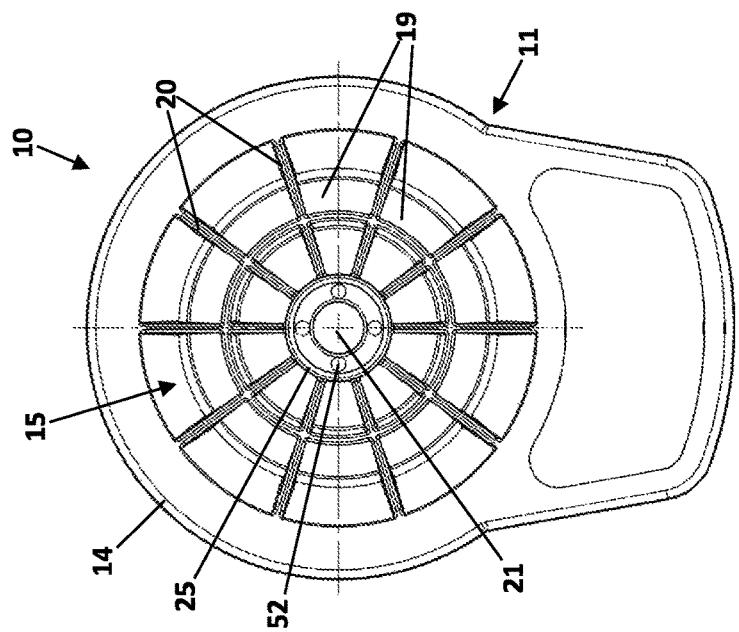
FIG. 3 depicts a rear plan view of an automotive air purifier according to an embodiment of the invention.
Figure 2:
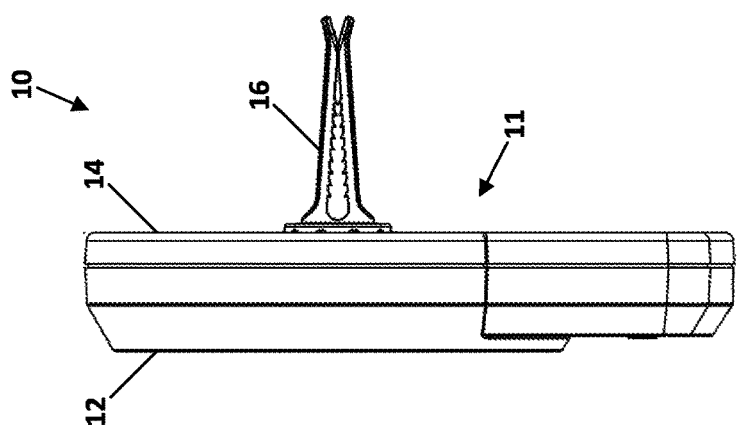
FIG. 2 depicts a side plan view of an automotive air purifier according to an embodiment of the invention.

FIGS. 1-4 depict an automotive air purifier 10 configured to be attached to a louver of an air vent of an automotive heating/cooling system. The purifier 10 includes a housing 11 comprising a front housing portion 12 that snaps together with a rear housing portion 14, and a louver clip 16 that snaps into an aperture 21 in the rear housing portion 14. In a preferred embodiment, the overall envelope of the housing 11 of the purifier 10 is about 4.5 inches high by about 3.5 inches wide by about 0.8 inch deep (excluding the clip). The louver clip 16 shown in FIG. 2 extends about 1.5 inches behind the rear housing portion 14. The front and rear housing portions 12 and 14 and the louver clip 16 are preferably formed from injection-molded polycarbonate having a UV stabilizer. Other views of the front and rear housing portions 12 and 14 are provided in FIGS. 7A-7B and 8A-8B. Other views of the louver clip 16 are provided in FIGS. 5A-5B.

Figure 1:
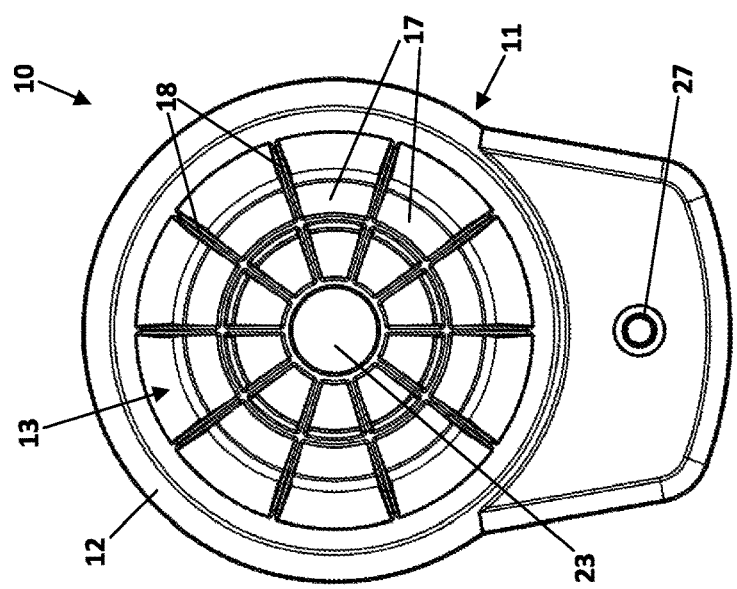
FIG. 1 depicts a front plan view of an automotive air purifier according to an embodiment of the invention.
Figure 7A:
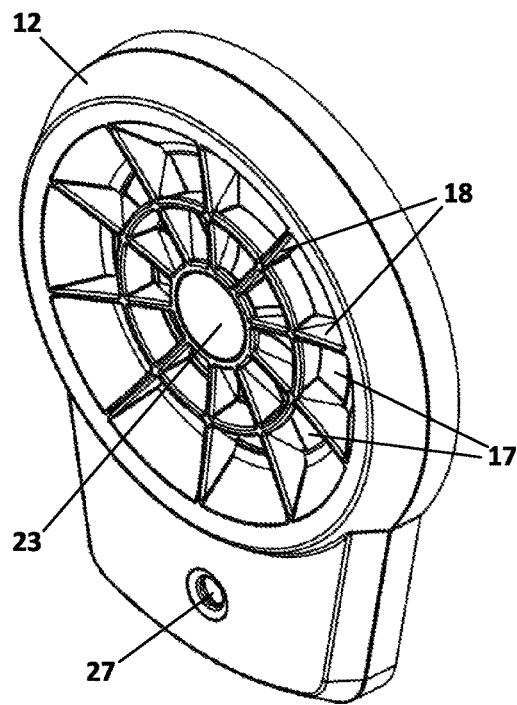
FIGS. 7A and 7B depict front and rear perspective views of a front housing portion of an automotive air purifier according to an embodiment of the invention.
Figure 7B:
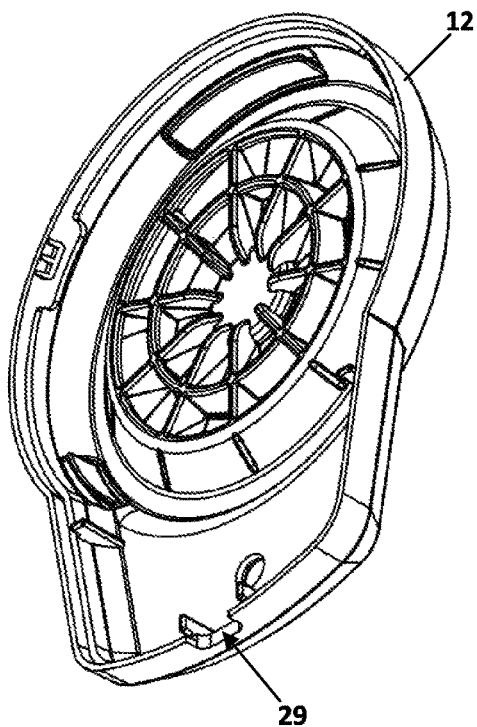

As shown in FIGS. 1 and 7A-7B, the front housing portion 12 has a front opening 13 through which air can flow. Spanning the front opening 13 are front radial vent spokes 18, the proximal ends of which connect to a front hub 23 near the center of the front opening 13. Between each adjacent pair of front vent spokes 18 are front airflow channels 17. The front housing portion 12 also has a central aperture 27 that receives a pushbutton switch 48 and a bottom aperture 29 that receives a USB connecter 50, both described in more detail hereinafter.

Figure 8A:
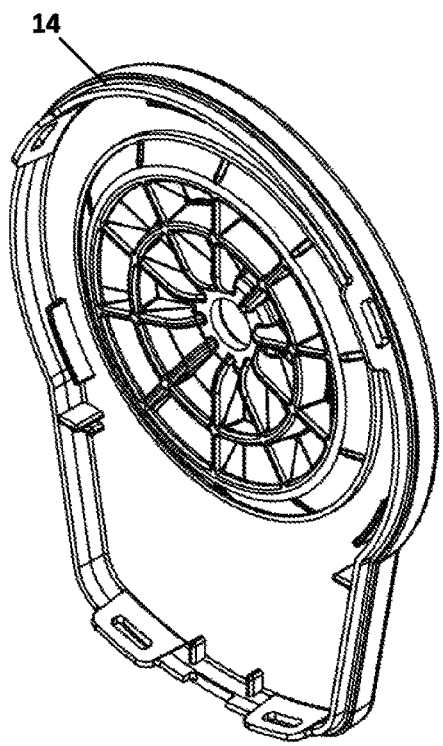
FIGS. 8A and 8B depict front and rear perspective views of a rear housing portion of an automotive air purifier according to an embodiment of the invention.
Figure 8B:
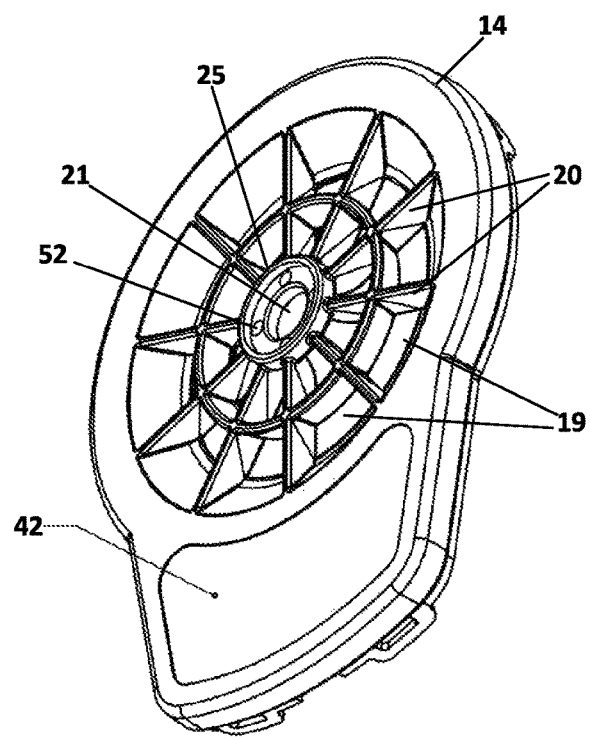

As shown in FIGS. 3 and 8A-8B, the rear housing portion 14 has a rear opening 15 through which air can flow. Spanning the rear opening 15 are rear radial vent spokes 20, the proximal ends of which connect to a rear hub 25 near the center of the rear opening 15. Between each adjacent pair of rear vent spokes 20 are rear airflow channels 19. A rear aperture 21 is provided in the rear hub 25.

Figure 4:
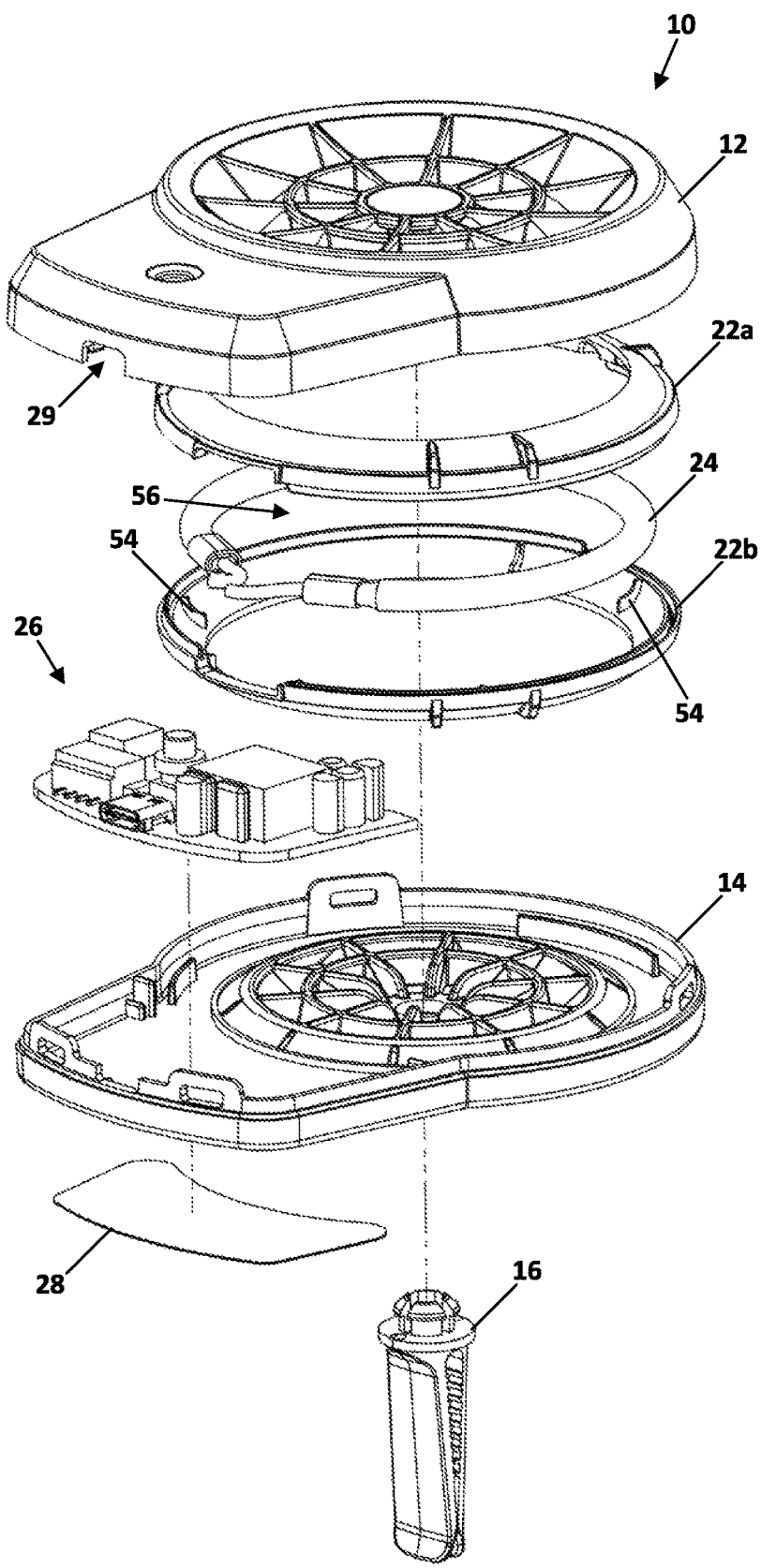
FIG. 4 is an exploded perspective view of an automotive air purifier according to an embodiment of the invention.
Figure 10:
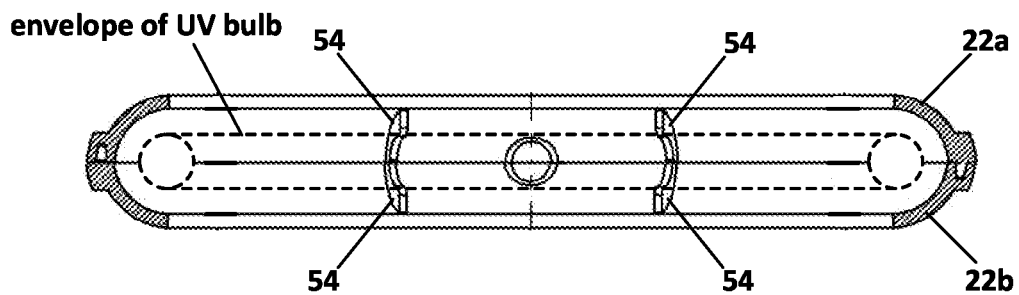
FIG. 10 is a cross-section view of rear and front UV reflectors of an automotive air purifier according to an embodiment of the invention.

As shown in FIG. 4, internal components of the purifier 10 include front and rear reflector portions 22a-22b, an annular UV bulb 24, and a printed circuit board assembly 26 containing electrical components described in more detail hereinafter. The reflector portions 22a-22b are preferably formed from injection-molded polycarbonate having a UV stabilizer. In the preferred embodiment, the inside surfaces 40 of the reflector portions 22a-22b (FIG. 6A) are coated with a UV-reflective mirror coating. Molded into the inside surfaces of the reflector portions 22a-22b are ribs 54 between which the UV bulb 24 is cradled. As shown in FIG. 4 and in the cross-section view of FIG. 10, the ribs 54 keep the UV bulb 24 secured and centered between the reflector portions 22a-22b. In a preferred embodiment, a label 28 may be attached to the exterior of the rear housing portion 14.

In the preferred embodiment, the annular UV bulb 24 is a model number DG-HC-5x70MM manufactured by Dongguan Huanchuang Technology Co., Ltd. This preferred bulb provides UV-C ultraviolet radiation in the 254 nm wavelength range, which is effective for sanitization. The central opening 56 in the UV bulb 24 has a diameter about 2.56 inches.

Details of the preferred embodiment of the louver clip 16 are depicted in FIGS. 5A and 5B. The louver clip 16 includes prongs 38 that are operable to flex inward somewhat as the tips of the prongs 38 are pressed into the aperture 21 in the rear housing portion 14. As the prongs 38 are pressed completely into the aperture 21, the flange 34 of the louver clip 16 engages the rear surface of the rear housing portion 14, and the prongs 38 snap outward to lock the louver clip 16 in place. The louver clip 16 includes a pair of opposing jaws 30 having ridges 32. The jaws 30 are operable to flex outward away from each other to engage a louver in one of the vehicle's heating/cooling vents, and the ridges 32 provide for additional friction to grip the louver.

A pair of opposing bumps 36 extending outward from the flange 34 of the louver clip 16 engage a corresponding opposing pair of depressions 52 molded into the surface of the hub 25 of the rear housing portion 14 (shown in FIGS. 3 and 8B). These mating bumps 36 and depressions 52 provide two selectable rotational positions of the louver clip 16—offset by 90 degrees—that may be selected depending on the rotational orientation of the louvers in the vehicle's heating/cooling vents.

Figure 9:
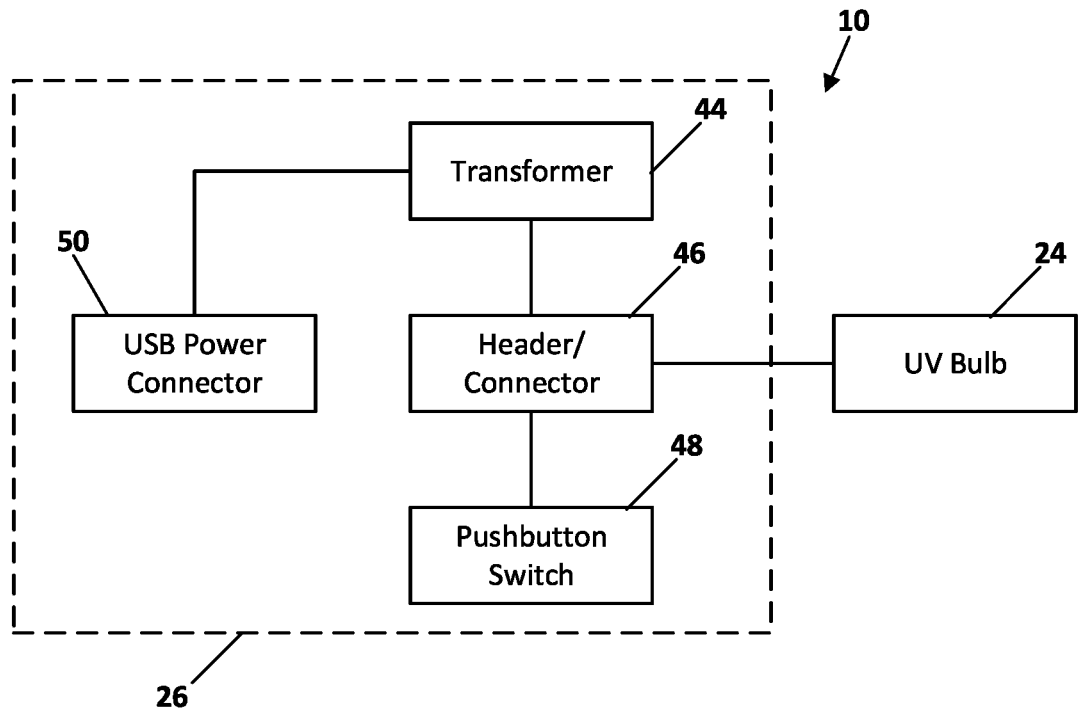
FIG. 9 is a functional block diagram of electrical components of an automotive air purifier according to an embodiment of the invention.

A functional block diagram of the electrical components of a preferred embodiment of the purifier 10 is depicted in FIG. 9. Power for the printed circuit board assembly 26 is preferably provided through a Universal Serial Bus (USB) type C shielded I/O surface mount connector 50, such as a Molex part number SD-105450-101. A transformer 44, such model number EFD15-640mH manufactured by Shenzhen Hedonglin Technology Co., Ltd, steps up the voltage from the USB connector 50 to about 206 volts for driving the UV bulb 24. A pushbutton switch 48, such as an E-Switch part number TL-3265-B-Q-S-CLR illuminated surface-mount SPST tact switch, is used to turn on/off power to the UV bulb 24. Power wires to the UV bulb 24 are connected to the printed circuit board assembly 26 via a surface-mount header/connector, such as Zhejiang Jieshital Electronic Co. part number A2501AWR-04-F2MA-R.

The purifier 10 is used by snapping the louver clip 16 onto a louver of one of the vehicle's heating/cooling vents, plugging in a USB power cord into the USB connector 50, and pressing and releasing the switch 48 to turn on the UV bulb 24. As the vehicle's heating/cooling system is turned on to initiate circulation of air in the vehicle, air from the vehicle vent flows into the channels 19 between the radial vent spokes 20 in the rear housing portion 14. The incoming air flows through the central opening 56 in the UV bulb 24 where the air is exposed to UV-C radiation from the bulb 24, which may come directly from the bulb or may be reflected from the mirrored surfaces 40 of the reflectors 22a-22b. The UV-C radiation damages the molecular structure of airborne viral microorganisms in the airflow, thereby rendering them harmless. The disinfected air then flows out of the channels 17 between the radial vent spokes 18 in the front housing portion 12, and into the cabin of the vehicle. The user can turn the UV bulb 24 off by pressing and releasing the switch 48 again.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An air purifier for use in a vehicle having louvered air vents, the air purifier comprising:
   a housing having a rear air flow opening and a front air flow opening that is aligned with and in air flow communication with the rear air flow opening;
   a louver clip attached to the housing adjacent the rear air flow opening, the louver clip configured to engage a louver on a louvered air vent in the vehicle and to hold the housing in place in front of the louvered air vent;

an annular ultraviolet light bulb disposed within the housing, the ultraviolet light bulb having a central air flow opening aligned with the front air flow opening and the rear air flow opening in the housing;

at least one annular ultraviolet reflector disposed within the housing that at least partially encircles the annular ultraviolet light bulb;

a power source disposed at least partially in the housing, the power source for providing electrical power to the ultraviolet light bulb; and a power switch disposed at least partially in the housing, the power switch for turning power on or off to the ultraviolet light bulb.

2. The air purifier of claim 1 further comprising:

the front air flow opening in the housing comprising a circular front air flow opening;

the rear air flow opening in the housing comprising a circular rear air flow opening;

a plurality of front radial vent spokes that span the circular front air flow opening in a radial pattern, wherein the circular front air flow opening is divided by the front radial vent spokes into a plurality of front air flow channels; and a plurality of rear radial vent spokes that span the circular rear air flow opening in a radial pattern, wherein the circular rear air flow opening is divided by the rear radial vent spokes into a plurality of rear air flow channels.

3. The air purifier of claim 2 further comprising:

a rear hub centrally disposed in the circular rear air flow opening of the housing, wherein proximal ends of the plurality of rear radial vent spokes terminate in the rear hub;

a central aperture centrally disposed through the rear hub; and the louver clip including a flange and a plurality of prongs extending forward of the flange, wherein the prongs are operable to flex inward as tips of the prongs are pressed into the central aperture of the rear hub, and wherein the prongs are operable to snap outward to secure the louver clip against the rear hub as the tips of the prongs pass through the central aperture.

4. The air purifier of claim 1 wherein the louver clip comprises a flange with a pair of opposing jaws extending rearward of the flange, wherein the opposing jaws are operable to flex outward away from each other to engage and clamp onto the louver in one of the air vents in the vehicle.

5. The air purifier of claim 1 wherein the least one annular ultraviolet reflector has a UV-reflective coating on inner surfaces thereof.

6. The air purifier of claim 1 wherein the least one annular ultraviolet reflector comprises front and rear reflector portions, and wherein the annular ultraviolet light bulb is sandwiched between the front and rear reflector portions.

7. The air purifier of claim 6 further comprising a plurality of ribs molded into inner surfaces of the front and rear reflector portions, wherein the ribs keep the annular ultraviolet light bulb secured and centered between the front and rear reflector portions.

8. The air purifier of claim 1 wherein the housing comprises:

a front housing portion in which the front air flow opening is disposed; and a rear housing portion in which the rear air flow opening is disposed, wherein the front and rear housing portions are operable to snap together to form the housing.

9. An air purifier for use in a vehicle having louvered air vents, the air purifier comprising:

a housing comprising:

a front housing portion comprising:

a front air flow opening;

a plurality of front radial vent spokes that span the front air flow opening in a radial pattern, such that the front air flow opening is divided by the front radial vent spokes into a plurality of front air flow channels; and a rear housing portion comprising:

a rear air flow opening that is aligned with and in air flow communication with the front air flow opening;

a plurality of rear radial vent spokes that span the rear air flow opening in a radial pattern, such that the rear air flow opening is divided by the rear radial vent spokes into a plurality of rear air flow channels, a rear hub centrally disposed within the rear air flow opening, wherein proximal ends of the plurality of rear radial vent spokes terminate in the rear hub; and a central aperture centrally disposed through the rear hub;

a louver clip attached to the rear housing portion adjacent the rear air flow opening, the louver clip configured to engage a louver on a louvered air vent in the vehicle and to hold the housing in place in front of the louvered air vent, the louver clip comprising:

a flange;

a plurality of prongs extending forward of the flange, wherein the prongs are operable to flex inward as tips of the prongs are pressed into the central aperture of the rear hub, and wherein the prongs are operable to snap outward to secure the louver clip against the rear hub as the tips of the prongs pass through the central aperture; and a pair of opposing jaws extending rearward of the flange, wherein the opposing jaws are operable to flex outward away from each other to engage and clamp onto the louver in one of the air vents in the vehicle;

an annular ultraviolet light bulb disposed within the housing, the ultraviolet light bulb having a central air flow opening aligned with and in air flow communication with the front air flow opening and the rear air flow opening in the housing;

at least one annular ultraviolet reflector disposed within the housing and at least partially encircling the annular ultraviolet light bulb, wherein the least one annular ultraviolet reflector comprises front and rear reflector portions, and wherein the annular ultraviolet light bulb is sandwiched between the front and rear reflector portions;

a power source disposed at least partially in the housing, the power source for providing electrical power to the ultraviolet light bulb; and a power switch disposed at least partially in the housing, the power switch for turning power on or off to the ultraviolet light bulb.

\* \* \* \* \*